(12) United States Patent
Doherty et al.

(10) Patent No.: US 6,414,130 B1
(45) Date of Patent: Jul. 2, 2002

(54) HER-2 BINDING ANTAGONISTS

(75) Inventors: Joni Kristin Doherty; Gail M. Clinton, both of Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 09/630,155

(22) Filed: Jul. 31, 2000

Related U.S. Application Data

(62) Division of application No. 09/234,208, filed on Jan. 20, 1999.

(51) Int. Cl.[7] .................. C07H 21/04; C07H 21/02; C12N 15/00; C12N 15/09; C12N 15/63
(52) U.S. Cl. .................. 536/23.5; 536/23.1; 435/320.1; 435/325; 435/69.1
(58) Field of Search .............................. 536/23.1, 23.5; 435/320.1, 325, 69.1

(56) References Cited

U.S. PATENT DOCUMENTS

| | | | |
|---|---|---|---|
| 5,401,638 A | 3/1995 | Carney et al. | 435/7.23 |
| 5,604,107 A | 2/1997 | Carney et al. | 435/7.23 |
| 5,720,937 A | 2/1998 | Hudziak et al. | 424/9.34 |
| 5,783,186 A | 7/1998 | Arakawa et al. | 424/143.1 |
| 6,015,567 A | 1/2000 | Hudziak et al. | 424/277.1 |

FOREIGN PATENT DOCUMENTS

| | | | |
|---|---|---|---|
| EP | 0412116 | 4/1989 | C12Q/1/68 |
| EP | 0494135 | 9/1989 | G01N/33/574 |

OTHER PUBLICATIONS

Bork, Genome Research, vol. 10, pp. 398–400, 2000.*
Bowie et al., Science vol. 247, pp. 1306–1310, Mar. 1990.*
Burgess et al., The Journal of Cell Biology, vol. 11, pp. 2129–2138, Nov. 1990.*
Lazar et al., Molecular and Cellular Biology, vol. 8, No. 3, pp. 1247–1252, Mar. 1988.*

"Circulatory HER2 extracellular domain (CCD) levels in Multiple Tumor Xenograft Models of HER-overexpressing Breast Cancer," Park, J.W., G. Colbern, A. Duijens, J. Baselga, D. Papahadjopoulos, C.C. Benz, UCSF, California; Geraldine Brush Cancer Research Institute, CPMC, SF, CA; Genentech, Inc. So. S.F., CA; Memorial Sloan–Kettering Cancer Center, NY, NY. (1997).

Christianson, Tracy A. et al., "NH$_2$ –terminally truncated HER–2/neu Protein: Relationship with Shedding of the Extracellular Domain and with Prognostic Factors in Breast Cancer," *Cancer Research* 58, 5123–5129, Nov. 15, 1998.

* cited by examiner

Primary Examiner—Sheela Huff
Assistant Examiner—Jennifer Hunt
(74) Attorney, Agent, or Firm—Barry L. Davison; Davis Wright Tremaine LLP

(57) ABSTRACT

There is disclosed a a pharmaceutical composition for treating solid tumors that overexpress HER-2, comprising an agent selected from the group consisting of (a) an isolated polypeptide having from about 50 to 79 amino acids taken from the sequence of SEQ ID NO. 1, wherein the polypeptide binds to the extracellular domain ECD of HER-2 at an affinity of at least $10^8$, (b) an isolated and glycosylated polypeptide having from about 300 to 419 amino acids taken from the sequence of SEQ ID NO. 2, wherein the C terminal 79 amino acids are present, and wherein at least three N-linked glycosylation sites are present, (c) a monoclonal antibody that binds to the ECD of HER-2, and (d) combinations thereof, with the proviso that the agent cannot be the monoclonal antibody alone, and pharmaceutically acceptable carrier.

7 Claims, 7 Drawing Sheets

A  Alternative HER-2 transcript containing ECDIIIa sequence

CCGGAGGTTACCCACTCACTGCTCCGAGGCCAGTGCAGTTCCTGCCCTCTGGCATGCCAGCCTGCCAGCCCACCCT 80
A R$^{340}$ G T H S L L P R P A A V P V P L R M Q P P A H P

81 GTCCTATCCTTCCTCAGAGACCCTCTTGGGACTTAGTCTCTGCTTCTACTCTCTGCCCCTCAGCCCCACACAAG 160
V L S F L R P S W D L V S A F Y S L P L A P L S P T S

161 TGTCCTATATCCCTGTCAGTGTGGGAGGGGAGACCCTGATGCTGTTAACCTGTCCCGGTATGAAG 240
V P I S P V S V G R G P D D A H V A V N L S R Y E

241 GCTGAGACGGCCCCCTGCCCACCCAGTGTCT
G$^{419}$ (stop)          V C T

5'  ATG   ECDIIIa
         insert
    nt 1171  1445                    AAA 3'

ECDIIIa HER-2 gene product:

N— I | II —341 419— ECD IIIa —C p185 HER-2 gene product:

N— I | II | III | IV —TM—KD—C

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 79
      (B) TYPE: amino acid
      (C) STRANDEDNESS: single
      (D) TOPOLOGY: unknown (ii) MOLECULE TYPE: HER-2 ECD antagonist (xi) SEQUENCE DESCRIPTION: SEQ ID NO: 1:

```
Gly Thr His Ser Leu Leu Pro Arg Pro Ala Ala Val Pro Val Pro Leu
                 5                  10                 15

Arg Met Gln Pro Gly Pro Ala His Pro Val Leu Ser Phe Leu Arg Pro
                20                  25                 30

Ser Trp Asp Leu Val Ser Ala Phe Tyr Ser Leu Pro Leu Ala Pro Leu
                35                  40                 45

Ser Pro Thr Ser Val Pro Ile Ser Pro Val Ser Val Gly Arg Gly Pro
 50                  55                  60

Asp Pro Asp Ala His Val Ala Val Asn Leu Ser Arg Tyr Glu Gly
 65                  70                  75
```

(2) INFORMATION FOR SEQ ID NO: 2:

(i) SEQUENCE CHARACTERISTICS:
        (A) LENGTH: 419
        (B) TYPE: amino acid
        (C) STRANDEDNESS: single
        (D) TOPOLOGY: unknown (ii) MOLECULE TYPE: polypeptide (xi) SEQUENCE DESCRIPTION: SEQ ID NO: 2:

```
Met Glu Leu Ala Ala Leu Cys Arg Trp Gly Leu Leu Leu Ala Leu Leu
                 5                  10                 15

Pro Pro Gly Ala Ala Ser Thr Gln Val Cys Thr Gly Thr Asp Met Lys
                20                  25                 30

Leu Arg Leu Pro Ala Ser Pro Glu Thr His Leu Asp Met Leu Arg His
                35                  40                 45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
 65                  70                  75                 80

Gln Gly Tyr Val Leu Ile Ala His Asn Gln Val Arg Gln Val Pro Leu
                85                  90                 95

Gln Arg Leu Arg Ile Val Arg Gly Thr Gln Leu Phe Glu Asp Asn Tyr
               100                 105                110

Ala Leu Ala Val Leu Asp Asn Gly Asp Pro Leu Asn Asn Thr Thr Pro
               115                 120                125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                160

Leu Cys Tyr Gln Asp Thr Ile Leu Trp Lys Asp Ile Phe His Lys Asn
                165                 170                175

Asn Gln Leu Ala Leu Thr Leu Ile Asp Thr Asn Arg Ser Arg Ala Cys
                180                 185                190

His Pro Cys Ser Pro Met Cys Lys Gly Ser Arg Cys Trp Gly Glu Ser
                195                 200                205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                240

Ala Ala Gly Cys Thr Gly Pro Lys His Ser Asp Cys Leu Ala Cys Leu
                245                 250                255

His Phe Asn His Ser Gly Ile Cys Glu Leu His Cys Pro Ala Leu Val
                260                 265                270
```

```
Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
        290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Gly Thr His Ser Leu Leu Pro Arg Pro Ala Ala Val
                340                 345                 350

Pro Val Pro Leu Arg Met Gln Pro Gly Pro Ala His Pro Val Leu Ser
        355                 360                 365

Phe Leu Arg Pro Ser Trp Asp Leu Val Ser Ala Phe Tyr Ser Leu Pro
        370                 375                 380

Leu Ala Pro Leu Ser Pro Thr Ser Val Pro Ile Ser Pro Val Ser Val
385                 390                 395                 400

Gly Arg Gly Pro Asp Pro Asp Ala His Val Ala Val Asn Leu Ser Arg
                405                 410                 415

Tyr Glu Gly
```

(2) INFORMATION FOR SEQ ID NO: 3:

(i) SEQUENCE CHARACTERISTICS:
        (A) LENGTH: 19
        (B) TYPE: nucleic acid
        (C) STRANDEDNESS: single
        (D) TOPOLOGY: unknown (ii) MOLECULE TYPE: oligonucleotide (xi) SEQUENCE DESCRIPTION: SEQ ID NO: 3:

TGAGCACCAT GGAGCTGGC                                          19

(2) INFORMATION FOR SEQ ID NO: 4:

(i) SEQUENCE CHARACTERISTICS:
        (A) LENGTH: 22
        (B) TYPE: nucleic acid
        (C) STRANDEDNESS: single
        (D) TOPOLOGY: unknown (ii) MOLECULE TYPE: oligonucleotide (xi) SEQUENCE DESCRIPTION: SEQ ID NO: 4:

TCCGGCAGAA ATGCCAGGCT CC                                    22

(2) INFORMATION FOR SEQ ID NO: 5:

(i) SEQUENCE CHARACTERISTICS:
        (A) LENGTH: 22
        (B) TYPE: nucleic acid
        (C) STRANDEDNESS: single
        (D) TOPOLOGY: unknown (ii) MOLECULE TYPE: oligonucleotide (xi) SEQUENCE DESCRIPTION: SEQ ID NO: 5:

AACACAGCGG TGTGAGAAGT GC                                    22

(2) INFORMATION FOR SEQ ID NO: 6:

(i) SEQUENCE CHARACTERISTICS:
        (A) LENGTH: 21

```
          (B) TYPE: nucleic acid
          (C) STRANDEDNESS: single
          (D) TOPOLOGY: unknown (ii) MOLECULE TYPE: oligonucleotide (xi) SEQUENCE DESCRIPTION: SEQ ID NO: 6:

ATACCGGGAC AGGTCAACAG C                                              21

(2) INFORMATION FOR SEQ ID NO: 7:

(i) SEQUENCE CHARACTERISTICS:
          (A) LENGTH: 20
          (B) TYPE: nucleic acid
          (C) STRANDEDNESS: single
          (D) TOPOLOGY: unknown (ii) MOLECULE TYPE: oligonucleotide (xi) SEQUENCE DESCRIPTION: SEQ ID NO: 7:

TCTGGGTACC CACTCACTGC                                                20

(2) INFORMATION FOR SEQ ID NO: 8:

(i) SEQUENCE CHARACTERISTICS:
          (A) LENGTH: 22
          (B) TYPE: nucleic acid
          (C) STRANDEDNESS: single
          (D) TOPOLOGY: unknown (ii) MOLECULE TYPE: oligonucleotide (xi) SEQUENCE DESCRIPTION: SEQ ID NO: 8:

TTCACACTGG CACGTCCAGA CC                                             22

(2) INFORMATION FOR SEQ ID NO: 9:

(i) SEQUENCE CHARACTERISTICS:
          (A) LENGTH: 27
          (B) TYPE: nucleic acid
          (C) STRANDEDNESS: single
          (D) TOPOLOGY: unknown (ii) MOLECULE TYPE: oligonucleotide (xi) SEQUENCE DESCRIPTION: SEQ ID NO: 9:

GCACGGATCC ATAGCAGACT GAGGAGG                                        27
```

HER-2 BINDING ANTAGONISTS

This application is a divisional application of Ser. No. 09/234,208, filed Jan. 20, 1999.

This work was supported by a grant from the Department of Defense (DOD) Breast Cancer Research Program. The United States Government has certain rights in this invention.

TECHNICAL FIELD OF THE INVENTION

The present invention provides a HER-2 binding antagonist. Specifically, intron retention has generated a novel HER-2 antagonist polypeptide that binds to the HER-2 receptor.

BACKGROUND OF THE INVENTION

The HER-2/neu (erbB-2) oncogene encodes a receptor-like tyrosine kinase (RTK) that has been extensively investigated because of its role in several human carcinomas (Hynes and Stern, Biochim. et Biophy. Acta 1198:165–184, 1994; and Dougall et al., Oncogene 9:2109–2123, 1994) and in mammalian development (Lee et al., Nature 378:394–398, 1995). The sequence of the HER-2 protein was determined from a cDNA that was cloned by homology to the epidermal growth factor receptor (EGFR) mRNA from placenta (Coussens et al., Science 230:1132–1139, 1985) and from a gastric carcinoma cell line (Yamamoto et al., Nature 319:230–234, 1986). The HER-2 mRNA was shown to be about 4.5 kb (Coussens et al., Science 230:1132–1139, 1985; and Yamamoto et al., Nature 319:230–234, 1986) and encodes a transmembrane glycoprotein of 185 kDa in normal and malignant human tissues (p185HER-2) (Hynes and Steen, Biochim. et Biophys. Acta 1198:165–184, 1994; and Dougall et al., Oncogene 9:2109–2123, 1994). The function of the HER-2 gene has been examined mainly by expressing the cDNA corresponding to the 4.5 kb transcript in transfected cells and from the structure and biochemical properties of the 185 kDa protein product. P185HER-2 consists of a large extracellular domain, a transmembrane segment, and an intracellular domain with tyrosine kinase activity (Hynes and Stern, Biochim. et Biophys. Acta 1198:165–184, 1994; and Dougall et al., Oncogene 9:2109–2123, 1994). Overexpression of p185HER-2 causes phenotypic transformation of cultured cells (DiFiore et al., Science 237:178–182, 1987; and Hudziak et al., Proc. Natl. Acad. Sci. USA 84:7159–7163, 1987) and has been associated with aggressive clinical progression of breast and ovarian cancer (Slamon et al., Science 235:177–182, 1987; and Slamon et al., Science 244:707–712, 1989). p185HER-2 is highly homologous to the EGFR. However, a ligand that directly binds with high affinity to p185HER-2 has not yet been identified. Moreover, the signaling activity of HER-2 may be mediated through heterodimerization with other ligand-binding members of the EGFR family (Carraway and Cantley, Cell 78:5–8, 1994; Earp et al., Breast Cancer Res. Treat. 35:115–132, 1995; and Qian et al., Oncogene 10:211–219, 1995).

Divergent proteins, containing regions of the extracellular domains of HER family RTKs, are generated through proteolytic processing of full length receptors (Lin and Clinton, Oncogene 6:639–643, 1991; Zabrecky et al., J. Biol. Chem. 266:1716–1720, 1991; Pupa et al., Oncogene 8:2917–2923, 1993; Vecchi et al., J. Biol. Chem. 271:18989–18995, 1996; and Vecchi and Carpenter, J. Cell Biol. 139:995–1003, 1997) and through alternative RNA processing (Petch et al., Mol. Cell. Biol. 10:2973–2982, 1990; Scott et al., Mol. Cell. Biol. 13:2247–2257, 1993; and Lee and Maihle, Oncogene 16:3243–3252, 1998). The extracellular domain of p185HER-2 is proteolytically shed from breast carcinoma cells in culture (Petch et al., Mol. Cell. Biol. 10:2973–2982, 1990; Scott et al., Mol. Cell. Biol. 13:2247–2257, 1993; and Lee and Maihle, Oncogene 16:3243–3252, 1998), and is found in the serum of some cancer patients (Leitzel et al., J. Clin. Oncol. 10:1436–1443, 1992) where it is may be a serum marker of metastatic breast cancer (Leitzel et al., J. Clin. Oncol. 10:1436–1443, 1992) and may allow escape of HER-2-rich tumors from immunological control (Baselga et al., J. Clin. Oncol. 14:737–744, 1966; and Brodowicz et al., Int. J. Cancer 73:875–879, 1997).

A truncated extracellular domain of HER-2 is also the product of a 2.3 kb alternative transcript generated by use of a polyadenylation signal within an intron (Scott et al., Mol. Cell. Biol. 13:2247–2257, 1993). The alternative transcript was first identified in the gastric carcinoma cell line, MKN7 (Yamamoto et al., Nature 319:230–234, 1986; and Scott et al., Mol. Cell. Biol. 13:2247–2257, 1993) and the truncated receptor was located within the perinuclear cytoplasm rather than secreted from these tumor cells (Scott et al., Mol. Cell. Biol. 13:2247–2257, 1993). However, no particular therapeutic, diagnostic or research utility has been ascribed to this truncated extracellular domain polypeptide. A truncated extracellular domain of the EGFR, generated by alternative splicing (Petch et al., Mol. Cell. Biol. 10:2973–2982, 1990) is secreted, exhibits ligand-binding, and dimerization properties (Basu et al., Mol. Cell. Biol. 9:671–677, 1989), and may have a dominant negative effect on receptor function (Basu et al., Mol. Cell. Biol. 9:671–677, 1989; and Flickinger et al., Mol. Cell. Biol. 12:883–893, 1992).

Therefore, there is a need in the art to find molecules that bind to cellular HER-2 and particularly molecules that bind to different sites than humanized antibodies to HER-2 (e.g., HERCEPTIN®. Such molecules would be useful therapeutic agents for various cancers that overexpress HER-2.

SUMMARY OF THE INVENTION

The present invention provides an isolated polypeptide having from about 50 to 79 amino acids taken from the sequence of SEQ ID NO. 1, wherein the polypeptide binds to the extracellular domain ECD of HER-2 at an affinity of at least $10^8$. Preferably, the isolated polypeptide is from about 69 to 79 amino acids in length. Preferably, the isolated polypeptide binds to a site on the ECD of HER-2 that is different from the site of binding of HERCEPTIN® (a marketed humanized monoclonal antibody that is used for the treatment of cancer and that binds to the ECD of HER-2).

The present invention further provides an isolated DNA sequence that codes on expression for a polypeptide having from about 50 to 79 amino acids taken from the sequence of SEQ ID NO. 1, wherein the polypeptide binds to the extracellular domain ECD of HER-2 at an affinity of at least $10^8$. Preferably, the isolated polypeptide is from about 69 to 79 amino acids in length. Preferably, the isolated polypeptide binds to a site on the ECD of HER-2 that is different from the site of binding of HERCEPTIN® (a marketed humanized monoclonal antibody that is used for the treatment of cancer and that binds to the ECD of HER-2). The present invention further provides a transfected cell comprising an expression vector having a DNA sequence that codes on expression for a polypeptide having from about 50 to 79 amino acids taken from the sequence of SEQ ID NO. 1, wherein the polypeptide binds to the extracellular domain ECD of HER-2 at an affinity of at least $10^8$.

The present invention further provides an isolated and glycosylated polypeptide having from about 80 to 419 amino acids taken from the sequence of SEQ ID NO. 2, wherein the C terminal 79 amino acids are present, and wherein at least three N-linked glycosylation sites are present. Preferably, the isolated polypeptide is from about 350 to 419 amino acids in length and four N-linked glycosylation sites are present. Preferably, the isolated polypeptide binds to a site on the ECD of HER-2 that is different from the site of binding of HERCEPTIN® (a marketed humanized monoclonal antibody that is used for the treatment of cancer and that binds to the ECD or HER-2).

The present invention further provides an isolated DNA sequence that codes on expression for a polypeptide having from about 80 to 419 amino acids taken from the sequence of SEQ ID NO. 3, wherein the C terminal 79 amino acids are present, and wherein at least three N-linked glycosylation sites are present. Preferably, the isolated polypeptide is from about 350 to 419 amino acids in length and four N-linked glycosylation are present. The present invention further provides a transfected cell comprising an expression vector having a DNA sequence that codes on expression for a polypeptide having from about 80 to 419 amino acids taken from the sequence of SEQ ID NO. 3, wherein the C terminal 79 amino acids are present, and wherein at least three N-linked glycosylation sites are present.

The present invention provides a method for treating a solid tumor characterized by overexpression of HER-2, comprising administering an agent that binds to the extracellular domain (ECD) of HER-2, wherein the agent is selected from the group consisting of (a) an isolated polypeptide having from about 50 to 79 amino acids taken from the sequence of SEQ ID NO. 1, wherein the polypeptide binds to the extracellular domain ECD of HER-2 at an affinity of at least $10^8$, (b) an isolated and glycosylated polypeptide having from about 80 to 419 amino acids taken from the sequence of SEQ ID NO. 2, wherein the C terminal 79 amino acids are present, and wherein at least three N-linked glycosylation sites are present, (c) a monoclonal antibody that binds to the ECD of HER-2, and (d) combinations thereof, with the proviso that the agent cannot be the monoclonal antibody alone. Preferably, the solid tumor that overexpresses HER-2 is selected from the group consisting of breast cancer, small cell lung carcinoma, ovarian cancer and colon cancer. Preferably, the agent is the isolated polypeptide having from about 50 to 79 amino acids taken from the sequence of SEQ ID NO. 1. Most preferably, the agent is a combination of the isolated polypeptide having from about 50 to 79 amino acids taken from the sequence of SEQ ID NO. 1 and the monoclonal antibody that binds to the ECD of HER-2.

The present invention further provides a pharmaceutical composition for treating tumors that overexpress HER-2, comprising an agent selected from the group consisting of (a) an isolated polypeptide having from about 50 to 79 amino acids taken from the sequence of SEQ ID NO. 1, wherein the polypeptide binds to the extracellular domain ECD of HER-2 at an affinity of at least $10^8$, (b) an isolated and glycosylated polypeptide having from about 80 to 419 amino acids taken from the sequence of SEQ ID NO. 2, wherein the C terminal 79 amino acids are present, and wherein at least three N-linked glycosylation sites are present, (c) a monoclonal antibody that binds to the ECD of HER-2, and (d) combinations thereof, with the proviso that the agent cannot be the monoclonal antibody alone, and pharmaceutically acceptable carrier. Preferably, the agent is the isolated polypeptide having from about 50 to 79 amino acids taken from the sequence of SEQ ID NO.1. Most preferably, the agent is a combination of the isolated polypeptide having from about 50 to 79 amino acids taken from the sequence of SEQ ID NO. 1 and the monoclonal antibody that binds to the ECD of HER-2.

The present invention further provides a method for targeting a therapeutic agent to solid tumor tissue, wherein the solid tumor tissue is characterized by overexpression of HER-2, comprising attaching the therapeutic agent to an isolated polypeptide having from about 50 to 79 amino acids taken from the sequence of SEQ ID NO. 1, wherein the polypeptide binds to the extracellular domain ECD of HER-2 at an affinity of at least $10^8$. Preferably, the isolated polypeptide is from about 69 to 79 amino acids in length. Preferably, the isolated polypeptide binds to a site on the ECD of HER-2 that is different from the site of binding of HERCEPTIN® (a marketed humanized monoclonal antibody that is used for the treatment of cancer and that binds to the ECD of HER-2).

The present invention further provides a method for determining the prognosis of tumor treatment for a tumor that overexpresses HER-2, comprising: (a) obtaining a bodily fluid, wherein the bodily fluid is selected from the group consisting of blood, serum, urine, lymph, saliva, tumor tissue, and combinations thereof; and (b) measuring the amount of p68HER-2 expressed using an anti-p68HER-2 antibody-based assay, wherein the assay is selected from the group consisting of ELISA, immunoprecipitation, immunohistocytochemistry, and Western analysis. Preferably, the method for determining the prognosis of tumor treatment further comprises measuring the amount of p185HER-2 ECD in the bodily fluid, and determining a ratio between the amount of p68HER-2 and p185HER-2.

BRIEF DESCRIPTION OF THE DRAWINGS

FIG. 1 shows a nucleotide sequence and amino acid of the insert in the extracellular domain of HER-2. The HER-2 ECD coding sequence from exon 1–9 (primers A and B) was amplified by PCR from a cDNA library from SKOV-3 cells. A product of ~1420 bp was found to be HER-2-specific by Southern blot analysis. This product was subcloned and the nucleotide sequence was determined. In panel A, the nucleotide sequence is shown for the 274 bp insert (outside the box) and for the immediately adjacent 5' and 3' sequences enclosed in the box. The insert is located between nucleotide residues 1171 and 1172 and following amino acid residue 340 in p185HER-2 using the numbering of Coussens et al. (*Science* 230:1132–1139, 1985). The consensus 5' and 3' splice sites at the arrows are shown in larger print. The inserted sequence is inframe with 5' HER-2 exon sequence and is deduced to encode a 79 amino acid extension following Arg 340 ($R^{340}$). The novel 79 novel amino acid sequence encoded by the insert is proline-rich (19%) and has a consensus asparagine linked glycosylation site, which is underlined. A stop codon was found at nucleotides 236–238 within the inserted sequence. In panel B, the predicted product of the alternative transcript is a truncated secreted protein which contains subdomains I and II identical to p185 and is missing the transmembrane domain and cytoplasmic domain. If fully glycosylated, the expected size is 65–70 kDa. This polypeptide product is referred to as p68HER-2. Thus, the product will be a truncated secreted protein which is missing the transmembrane domain and cytoplasmic domain found in p185HER-2.

DETAILED DESCRIPTION OF THE INVENTION

Figure 2:
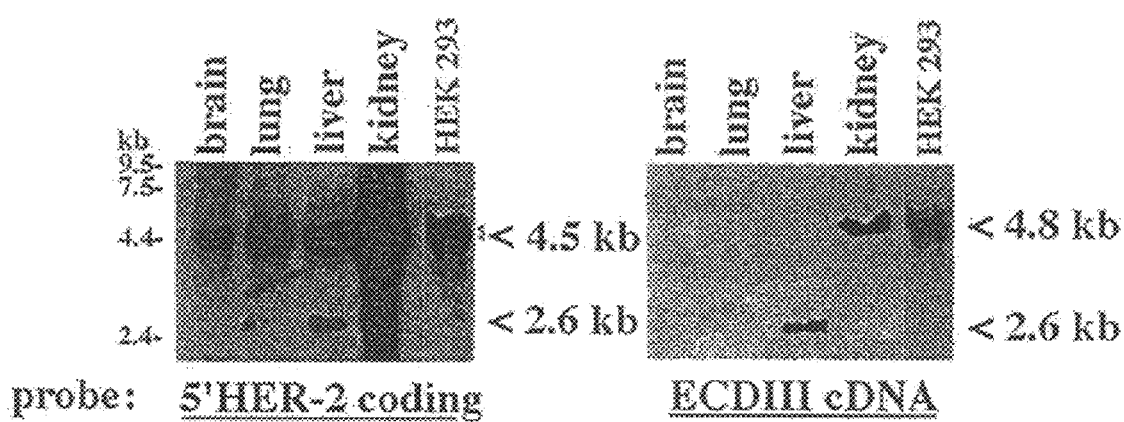
FIG. 2 shows the detection of alternative HER-2 transcripts containing the ECDIIIa sequence by Northern blot analysis. PolyA+mRNA (2.5 μg) from different human fetal tissues (Clontech) or isolated from HEK-293 cells was resolved in a formalin agarose gel and transferred to a BRIGHTSTAR® membrane (Ambion) in 10×SSC. The membrane was hybridized with a $^{32}$P-labeled antisense RNA probe complimentary to the ECDIII sequence, stripped and reprobed with a $^{32}$P labeled cDNA probe specific for the 5' HER-2 exon sequence. The membranes were washed under high stringency conditions and analyzed by phosphorimaging (Molecular Dynamics).

The present invention is based upon the initial discovery of an alternative HER-2 mRNA of 4.8 kb with a 274 bp insert identified as intron 8. The retained intron is in-frame and encodes 79 amino acids [SEQ ID NO. 1] followed by a stop codon at nucleotide 236. The alternative mRNA predicts a truncated HER-2 protein that lacks the transmembrane and intracellular domains and contains 419 amino acids [SEQ ID NO. 2]; 340 residues that are identical to the N-terminus of p185HER-2 and 79 unique residues at the C-terminus [SEQ ID NO. 1]. Using specific antibodies against either the novel 79 amino acid residue C-terminal sequence [SEQ ID NO. 1] or the N-terminus of p185HER-2, a 68 kDa protein product was identified [SEQ ID NO.2]. This 68 kDa protein product is an alternative HER-2 transcript in cell extracts and in extracellular media from several cell lines. Expression of the alternative transcript was highest in a nontransfected human embryonic kidney cell line.

Figure 3:
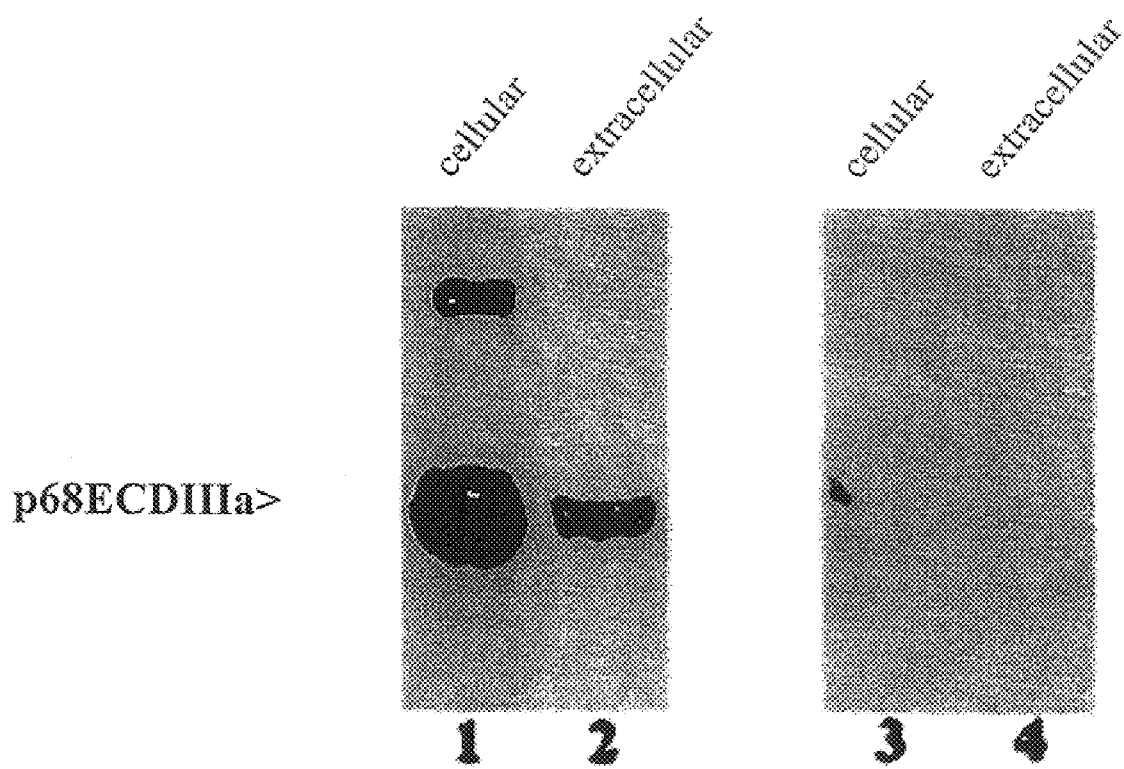
FIG. 3 shows a sequence-specific reactivity of anti-ECDIIIa with a protein of ~68 kDa in a human embryonic kidney cell line (HEK293). Cell extract protein (20 μg) and 20 μl of media conditioned by HEK-293 cells were Western blotted and probed with anti-ECDIIIa diluted 1:10,000 (lanes 1 and 2) or with anti-ECDIIa diluted 1:10,000 containing 50 μg/ml purified His-tagged ECDIIIa peptide (lanes 3, 4).
Figure 5:
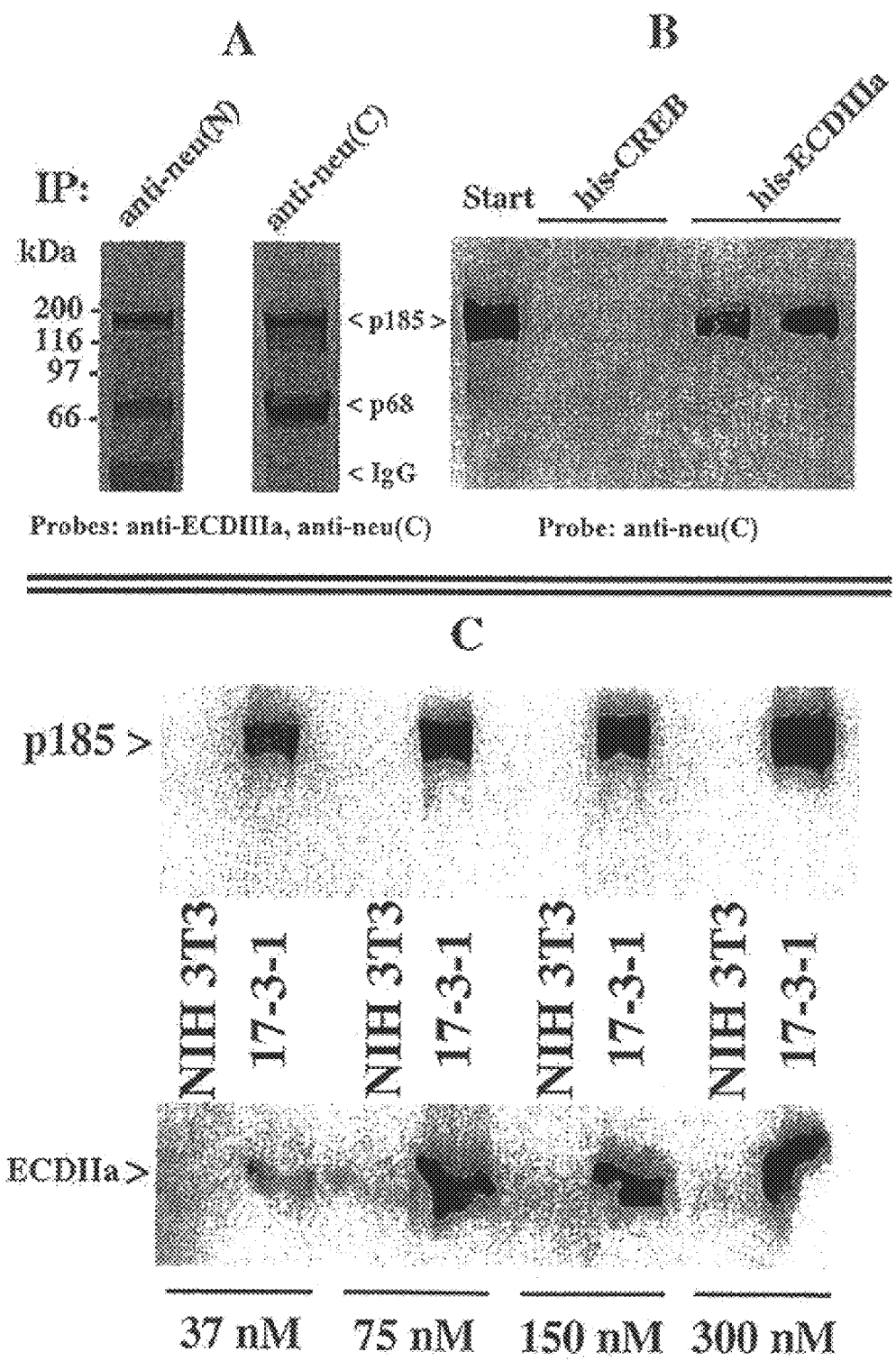
FIG. 5 shows that p68ECDIIIa binds to p185HER-2. In panel A: Two mg of SKBR-3 cells extracted in nondenaturing buffer were immunoprecipitated with 5 μl anti-neu(N) specific for the N-terminal sequence of p68HER-2 and p185HER-2, or with 5 μl anti-neu(C) specific for the C-terminus of p185HER-2 and then probed as a Western blot with both anti-ECDIIIa specific for p68HER-2 and with anti-neu(C) specific for p185HER-2. In panel B: 100 μg of 17-3-1 cell extract were incubated in duplicate with 50 μl packed volume of NiNTA agarose (Qiagen) coupled to 20 μg of His-tagged ECDIIIa or to 20 μg His-tagged CREB fragment in 200 μl of wash buffer (20 mM Tris pH 8.0, 300 mM NaCl) at room temperature for 1 hr with shaking. The resin was then washed 4 times with 500 μl of wash buffer and proteins were eluted by incubation with 50 μl SDS-sample buffer at 100° C. for 2 min. Eluted proteins were analyzed by Western blot analysis using antibodies against the C-terminus of p185HER-2, anti-neu(C). In panel C: Monolayers of ~10$^5$ 3T3 cells or HER-2 transfected 17-3-1 cells in 12 well plates were washed twice with PBS and then incubated with 0.5 ml of serum-free media with 1% BSA and 39, 75, 150, and 300 nM of purified recombinant His-tagged ECDIIIa for 2 hrs at 4° C. Cells were washed 1 time in PBS containing 1% BSA and twice in PBS and then were extracted in denaturing buffer. Equal aliquots (20 μg protein) were analyzed by western blotting with antibodies specific for ECDIIIa (anti-ECDIIIa) or, in the upper panel, with antibodies specific for p185HER-2 (anti-neu(C)).

The results presented here show expression of alternative HER-2 mRNA, which contains an additional 274 nucleotides, probably intron 8. Consistent with this finding, an alternative transcript of ~4.8 kb was detected in human fetal kidney tissue and in the human embryonic kidney cell line, HEK 293. Moreover, a transcript of 2.6 kb, which is the size expected if the sequence is retained in the 2.3 kb truncated HER-2 mRNA (Yamamoto et al., *Nature* 319:230–234, 1986; and Scott et al., *Mol. Cell. Biol.* 13:2247–2257, 1993), was detected in human fetal liver tissue by Northern blot analysis using a probe specific for the inserted sequence or for the HER-2 ECD coding sequence (FIG. 2). The inserted sequence introduces a termination codon and predicts a novel 79 amino acid extension designated ECDIIIa at residue 340 of the p185HER-2 protein. The predicted protein therefore lacks the transmembrane and intracellular domains, but contains subdomains I and II of the extracellular domain of p185HER-2. As predicted, a secreted protein which contains N-terminal sequence of p185HER-2 and the C-terminal extension provided by the inclusion of the novel sequence was detected (FIGS. 3 and 5). The ECDIIIa protein was found to be 68 kDa which is the approximate size expected of the protein encoded by the alternative transcript if the five N-linked glycosylation sites found in subdomains I and II of p185HER-2 are glycosylated (Stern et al., *Mol. Cell. Biol.* 6:1729–1740, 1986).

The data presented herein demonstrate that p68HER-2 specifically binds to p185HER-2. The association with p185HER-2 may be conferred by the novel proline rich ECDIIIa domain rather than the N-terminal subdomains I and II of p68HER-2. While the HER-2 ECD, generated by in vitro deletion mutagenesis, also contains subdomains I and II, it does not associate with the extracellular domain of p185HER-2 unless engineered to enhance their proximity (Tzahar et al., *EMBO J.* 16:4938–4950, 1997; O'Rourke et al., *Proc. Natl. Acad. Sci. USA* 94:3250–3255, 1997; and Fitzpatrick et al., *FEBS Letters* 431:102–106, 1998). However, the unique ECDIIIa peptide binds with high affinity (nM concentrations) to p185HER-2 and to transfected 17-3-1 cells that overexpress p185HER-2 (FIG. 5). Preferential binding of the ECDIIIa domain peptide to 17-3-1 cells indicates that secreted p68HER-2 interacts with the extracellular region of p185HER-2 at the cell surface. Therefore, p68HER-2 and fragments thereof appear to be a naturally occurring HER-2 binding protein, encoded by the HER-2 gene. In contrast to EGFR family ligands (Groenen et al., *Growth Factors* 11:235–257, 1994), p68HER-2 lacks an EGF homology domain and contains the first 340 amino acids of the receptor itself, p185HER.

Previously described putative HER-2 ligands were found to associate indirectly with p185HER-2 only in a heterodimer with an EGFR family member (Heldin and Ostman, *Cytokine Growth Factor Rev.* 7:33–40, 1996). Although it is possible that ECDIIIa binds indirectly to p185HER-2 through a coreceptor, this seems unlikely since detergent solubilized p185HER-2 was specifically and efficiently "pulled down" by immobilized ECDIIIa peptide (FIG. 5B).

For all naturally occurring or engineered ligands for mammalian EGFR family members, binding is tightly coupled to stimulation of receptor dimerization and tyrosine phosphorylation (Hynes and Stern, *Biochim. et Biophys. Acta* 1198:165–184, 1994: Dougall et al., *Oncogene* 9:2109–2123, 1994; and Groenen et al., *Growth Factors* 11:235–257, 1994). Although they bind, neither p68HER-2 nor the ECDIIIa peptide was found to activate p185HER-2. Activation was assessed in two different cell lines that differ in the extent of p185HER-2 tyrosine phosphorylation, transfected 17-3-1 cells as well as SKOV-3 ovarian carcinoma cells. Furthermore in vitro self-phosphorylation activity, which is enhanced in dimeric forms of p185HER-2 (Dougall et al., *Oncogene* 9:2109–2123, 1994; and Lin et al., *J. Cell. Biochem.* 49, 290–295, 1992), was not stimulated by p68HER-2 or ECDIIIa. Similarly, the Argos protein, which is an extracellular inhibitor of the Drosophila EGF receptor and the only known antagonist of class I RTKs, did not simulate tyrosine phosphorylation of the receptor (Schweitzer et al., *Nature* 376:699–702, 1995). Likewise, Angiopoietin-2, a natural antagonist for the Tie 2 RTK, bound the endothelial receptor but failed to activate it (Maisonpierre et al., *Science* 277:55–60, 1997).

Without being bound by theory, since p68HER-2 occupies but does not activate, it could block dimerization of p185HR-2. By analogy, HER-2 ECD, when engineered to enhance its binding to RTKs, prevented the formation of productive dimers required for transphosphorylation and receptor activation thereby having a dominant negative effect (O'Rourke et al., *Proc. Natl. Acad. Sci. USA* 94:3250–3255, 1997). In contrast to the HER-2 ECD, soluble p68HER-2 exhibited strong binding to p185HER-2, yet also contains subdomain I and II of the ECD. Since subdomain I may be the low affinity, promiscuous ligand binding site required for recruitment of p185HER-2 into heteromeric complexes (Tzahar et al., *EMBO J.* 16:4938–4950, 1997), p68HER-2 could block this site and thereby obstruct recruitment of p185HER-2 into dimers. Alternatively, p68HER-2 could compete with an uncharacterized ligand for binding to p185HER-2. The tissue-specific expression of p68HER-2 in human fetal liver and kidney may function to modulate the extent to which p185HER-2 is occupied during development of these organs. Moreover, the overexpression of p185HER-2, relative to p68HER-2 in tumor cells with HER-2 gene amplification (FIG. 3), could occur though a selective pressure based on overcoming the effects of a binding protein such as p68HER-2. Therefore, p68HER-2 is the first example of a naturally occurring p185HER-2 binding protein that may prevent activation of p185HER-2.

Pharmaceutical Composition

The present invention further provides a pharmaceutical composition for treating solid tumors that overexpress HER-2, comprising an agent selected from the group consisting of (a) an isolated polypeptide having from about 50 to 79 amino acids taken from the sequence of SEQ ID NO. 1, wherein the polypeptide binds to the extracellular domain ECD of HER-2 at an affinity of at least $10^8$, (b) an isolated and glycosylated polypeptide having from about 300 to 419 amino acids taken from the sequence of SEQ ID NO. 2, wherein the C terminal 79 amino acids are present, and wherein at least three N-linked glycosylation sites are present, (c) a monoclonal antibody that binds to the ECD of HER-2, and (d) combinations thereof, with the proviso that the agent cannot be the monoclonal antibody alone, and pharmaceutically acceptable carrier. Preferably, the agent is the isolated polypeptide having from about 50 to 79 amino acids taken from the sequence of SEQ ID NO. 1. Most preferably, the agent is a combination of the isolated polypeptide having from about 50 to 79 amino acids taken from the sequence of SEQ ID NO. 1 and the monoclonal antibody that binds to the ECD of HER-2.

The inventive pharmaceutical composition, comprising either or both of the inventive polypeptides and/or monoclonal antibody, can be administered to a patient either by itself (complex or combination) or in pharmaceutical compositions where it is mixed with suitable carriers and excipients. Inventive polypeptide can be administered parenterally, such as by intravenous injection or infusion, intraperitoneal injection, subcutaneous injection, or intramuscular injection. Inventive polypeptide can be administered orally or rectally through appropriate formulation with carriers and excipients to form tablets, pills, capsules, liquids, gels, syrups, slurries, suspensions and the like. Inventive polypeptide can be administered topically, such as by skin patch, to achieve consistent systemic levels of active agent. Inventive polypeptide is formulated into topical creams, skin or mucosal patch, liquids or gels suitable to topical application to skin or mucosal membrane surfaces. Inventive polypeptide can be administered by inhaler to the respiratory tract for local or systemic treatment of cancers characterized by overexpressing HER-2.

The dosage of inventive polypeptide suitable for use with the present invention can be determined by those skilled in the art from this disclosure. Inventive polypeptide will contain an effective dosage (depending upon the route of administration and pharmacokinetics of the active agent) of inventive polypeptide and suitable pharmaceutical carriers and excipients, which are suitable for the particular route of administration of the formulation (i.e., oral, parenteral, topical or by inhalation). The active inventive polypeptide is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the inventive polypeptide in water-soluble form. Additionally, suspensions of the inventive polypeptide may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

Pharmaceutical formulations for oral administration can be obtained by combining the active compound with solid excipients, such as sugars (e.g., lactose, sucrose, mannitol or sorbitol), cellulose preparations (e.g., starch, methyl cellulose, hydroxypropylmethyl cellulose, and sodium carboxymethyl cellulose), gelaten, gums, or polyvinylpyrrolidone. In addition, a desintegrating agent may be added, and a stabilizer may be added.

Processes for Synthesizing p68 and 79 aa C Terminal Region

Polypeptide synthesis is done by a group of standard procedures for polypeptide synthesis by sequential amino acids building through peptide synthesis equipment, following manufacturer's instructions for synthesizing peptides. Preferably, shorter polypeptides, of less than 100 amino acids, are best suited for the method of synthesis through sequential amino acid building of polypeptides. In addition, heterologous polypeptides can be expressed by transformed cells using standard recombinant DNA techniques to transform either prokaryotic or eukaryotic cells, provide appropriate growth media for their expression, and then purify the inventive polypeptide either from the media or from intracellular contents depending upon the type of cell used and its expression characteristics.

Methods for Treating Cancer with p68, 79 aa C Terminal Region, and Combinations

The present invention provides a method for treating a solid tumor characterized by overexpression of HER-2, comprising administering an agent that binds to the extracellular domain (ECD) of HER-2, wherein the agent is selected from the group consisting of (a) an isolated polypeptide having from about 50 to 79 amino acids taken from the sequence of SEQ ID NO. 1, wherein the polypeptide binds to the extracellular domain ECD of HER-2 at an affinity of at least $10^8$, (b) an isolated and glycosylated polypeptide having from about 300 to 419 amino acids taken from the sequence of SEQ ID NO. 2, wherein the C terminal 79 amino acids are present, and wherein at least three N-linked glycosylation sites are present, (c) a monoclonal antibody that binds to the ECD of HER-2, and (d) combinations thereof, with the proviso that the agent cannot be the monoclonal antibody alone. Preferably, the solid tumor that overexpresses HER-2 is selected from the group consisting of breast cancer, small cell lung carcinoma, ovarian cancer, prostate cancer, gastric cancinoma, cervical cancer, esophageal cancinoma, and colon cancer. Preferably, the agent is the isolated polypeptide having from about 50 to 79 amino acids taken from the sequence of SEQ ID NO. 1. Most preferably, the agent is a combination of the isolated polypeptide having from about 50 to 79 amino acids taken from the sequence of SEQ ID NO. 1 and the monoclonal antibody that binds to the ECD of HER-2.

The p68HER-2 polypeptide described herein was found to bind to HER-2 and prevent signal transduction through the kinase domain. Without being bound by theory, the unique ECDIIIa domain mediates specific binding to p185HER-2 and the resulting interaction with p68ECDIIIa prevents p185HER-2 dimerization and subsequent signal transduction. Therefore, p68HER-2 functions as a HER-2 antagonist to prevent signal transduction by preventing dimerization as a necessary prerequisite for signal transduction. Thus, the mechanism of p68HER-2 as a HER-2 antagonist is different from the mechanism of binding agents, such as the 79 amino acid polypeptide described herein or a monoclonal antibody that binds to the EDC of HER-2. The inventive method provides that p68HER-2 inhibits tumor cell growth in tumors that overexpress HER-2 by providing a selective pressure for such tumor cells. Similarly, the HER-2 antagonists that are binding agents also inhibit tumor cell growth in tumors that overexpress HER-2 by providing selective pressure to such cells to prevent ligand binding to the ECD of HER-2 and prevent signal transduction even before potential dimerization.

Use of 79 aa C Terminal Region as a Targeting Molecule

The present invention further provides a method for targeting a therapeutic agent to solid tumor tissue, wherein the solid tumor tissue is characterized by overexpression of HER-2, comprising attaching the therapeutic agent to an isolated polypeptide having from about 50 to 79 amino acids taken from the sequence of SEQ ID NO. 1, wherein the polypeptide binds to the extracellular domain ECD of HER-2 at an affinity of at least $10^8$. Preferably, the isolated polypeptide is from about 69 to 79 amino acids in length. Preferably, the isolated polypeptide binds to a site on the ECD of HER-2 that is different from the site of binding of HERCEPTIN® (a marketed humanized monoclonal antibody that is used for the treatment of cancer and that binds to the ECD or HER-2). It was discovered that the 79 amino acid polypeptide [SEQ ID NO. 1] exhibited surprising high affinity binding properties to the ECD of HER-2. Moreover, the site of such binding is different and unaffected by the site of binding of a marketed humanized monoclonal antibody (HERCEPTIN®). Therefore, the high binding affinity enables the 79 amino acid polypeptide to function as a targeting molecule to tumor cells expressing HER-2.

Anti-p68 Antibody as a Diagnostic/Prognostic Agent

The p68HER-2 glycosylated polypeptide was expressed and used as an antigen for antibody production. Specifically, antibody specific for p68HER-2 was prepared by injecting rabbits with purified polyhistidine-tagged ECDIIIa peptide, which is the same as the intron encoded novel C-terminus or p68HER-2, the domain that binds with high affinity to p185HER-2. The isolated polyclonal antibody detected pM quantities of ECDIIIa peptide or of p68HER-2 with high specificity (see FIGS. 3 and 5). Thus, an antibody specific for p68HER-2 is useful as a diagnostic agent for detecting p68HER-2 in bodily fluids and tumor tissues using diagnostic techniques, such as ELISA, immunoprecipitation, immunohistochemistry or Western analysis.

Accordingly, the present invention further provides a method for determining the prognosis of tumor treatment for a tumor that overexpresses HER-2, comprising: (a) obtaining a bodily fluid, wherein the bodily fluid is selected from the group consisting of blood, serum, urine, lymph, saliva, tumor tissue, and combinations thereof; and (b) measuring the amount of p68HER-2 expressed using an anti-p68HER-2 antibody-based assay, wherein the assay is selected from the group consisting of ELISA, immunoprecipitation, immunohistocytochemistry, and Western analysis. Preferably, the method for determining the prognosis of tumor treatment further comprises measuring the amount of p185HER-2 ECD in the bodily fluid, and determining a ratio between the amount of p68HER-2 and p185HER-2. The higher the ratio of p68HER-2:p185HER-2, the better the treatment prognosis.

P68HER-2 as a Therapeutic Agent

Without being bound by theory, but it appears that p68HER-2 or ECDIIIa peptide inhibits the growth of tumor cells that overexpress HER-2 by binding to p185HER-2 at the cells surface. This hypothesis was examined by testing anchorage independent growth of cells in the presence or absence of p68HER-2 using cells that depend on p185HER-2 overexpression for their malignant growth, yet have little or no detectable p68HER-2. Anchorage independent growth of cells in soft agar was used as a predictive model for tumor cytotoxicity. This is a common and predictive procedure to examine transforming activity and reflects the tumorigenic and oncogenic potential of cells (DiFore et al., Science 237:178–182, 1987; Hudziak et al., Proc. Natl. Acad. Sci. USA 84:7159–7163, 1987; and Baasner et al., Oncogene 13:901–911, 1996).

Figure 7:
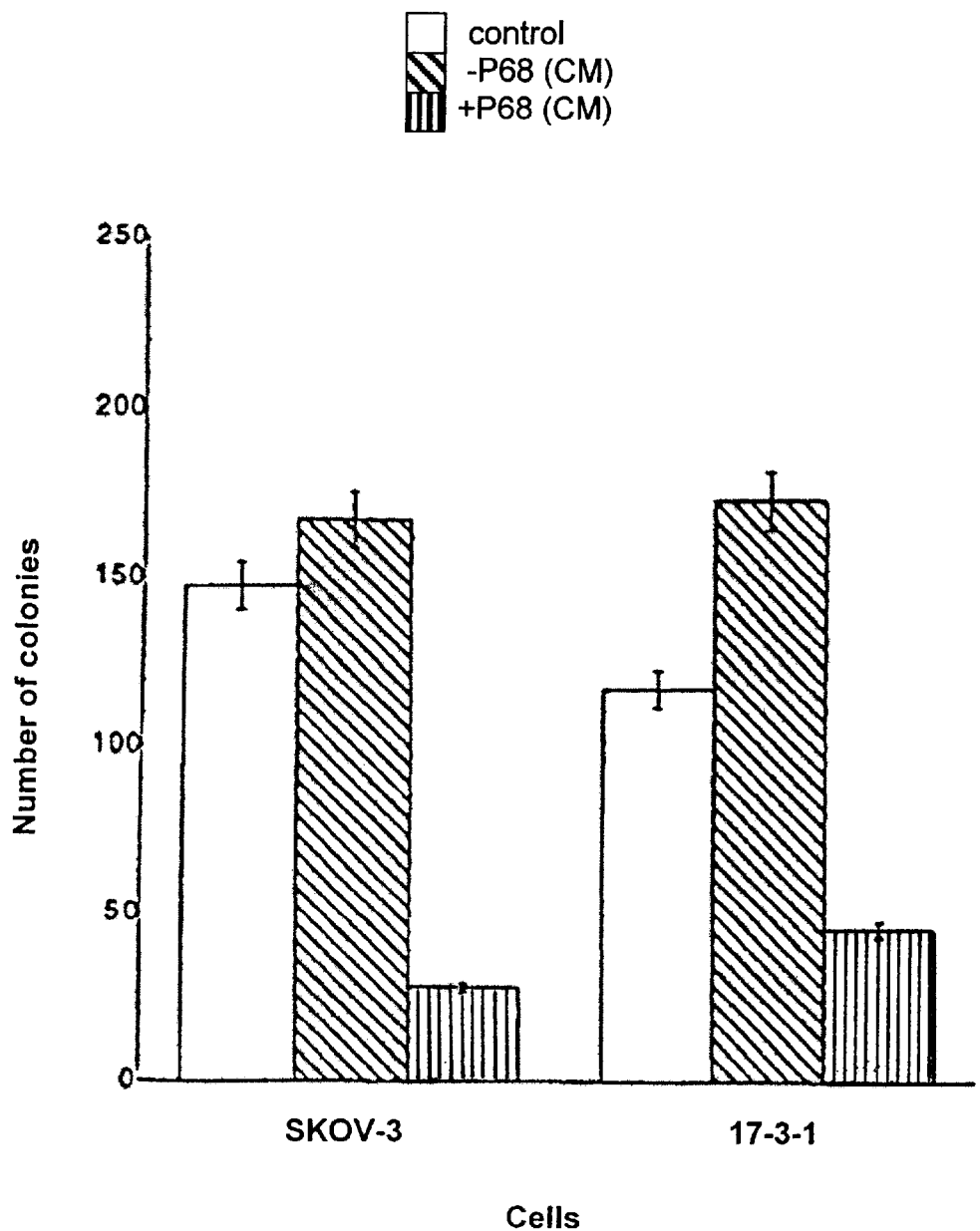
FIG. 7 shows that p68HER-2 inhibited anchorage independent growth of tumorigenic cells. SKOV-3 ovarian carcinoma cells and HER-2 transfected 17-3-1 cells were suspended in media with 10% fetal bovine serum containing 0.3% agar (control conditions) to which was added 50×concentrated media conditioned by SKOV-3 cells (which contains no detectable p68HER-2 (−p68 CM)), or 50×concentrated media conditioned by HEK-293 cells (which contains 20 nM p68HER-2 (+p68CM)). Five times 10$^3$ cells were plated in triplicate for each experimental condition onto a 0.5 ml layer of media containing 0.5% agarose in 12 well plates. The results shown are plotted as the mean and standard deviation of the number of colonies with more than 50 cells in triplicate wells counted at 21 days of incubation. Similar results were observed in three separate experiments.

The effects of p68HER-2 on anchorage independent growth in soft agar was determined using SKOV-3 carcinoma cells and HER-2 transfected 17-3-1 cells, which are both tumorigenic and overexpress p185HER-2. The cells were suspended in media supplemented with fetal calf serum in the presence or absence of p68HER-2 and incubated for 21 days in a humidified incubator. Anchorage independent growth was quantitated by counting the number of colonies that contained more than 50 cells. FIG. 7 shows that in the presence of p68HER-2, anchorage independent growth of both SKOV-3 cells and 17-3-1 cells was inhibited several fold. Accordingly, these data show that p68HER-2 is not just cytostatic, but cytotoxic and possibly apoptotic.

EXAMPLE 1

This example provides the results from an experiment to investigate HER-2 mRNA diversity within the extracellular domain (ECD) coding sequence using polymerase chain reaction (PCR). A cDNA library from SKOV-3 cells (American Type Culture Collection (Rockville, Md.) maintained in DMEM, supplemented with 10% fetal bovine serum and 0.05% gentamycin), an ovarian carcinoma cell line in which the HER-2 gene is amplified eight times (Tyson et al., Am. J. Obstet. Gynecol. 165:640–646, 1991) was examined using a forward primer specific for exon 1 (Tal et al., Mol. Cell. Biol. 7, 2597–2601, 1987) identical to nucleotides 142–161 and a reverse primer complementary to nucleotides 1265–1286 in exon 9 (Scott et al., Mol. Cell. Biol. 13:2247–2257, 1993). Briefly, The SKOV-3 cDNA library was provided by Origene Technologies, Inc. (Rockville, Md.), and was prepared from RNA extracted from SKOV-3 cells. RNA was extracted from SKOV-3 cells grown to 80% confluence on 15 cm plates with TriReagent (Molecular Research Center, Inc., Cincinnati, Ohio.), according to the manufacturer's protocol, to obtain total RNA. RNA was resuspended in 10 mM Tris-EDTA, pH 8.0, for reverse transcription and cDNA library construction, or in RNA hybridization buffer (80% formamide, 40 mM PIPES, 4 mM NaCl, 1 mM EDTA, pH 7.5) for ribonuclease protection assay (RPA). RNA concentrations were determined spectrophotometrically at $OD_{260}$. Poly $A^+$mRNA was selected from total RNA using a mRNA extraction kit (Oligotex, Qiagen).

A product of ~1420 bp, determined to be HER-2-specific by Southern blotting, was approximately 270 bp larger than the expected size of 1144 bp from the previously described cDNA sequence (Coussens et al., Science 230:1132–1139, 1985). Briefly, the Southern blotting procedure transferred nucleic acids from agarose gels under vacuum (Bio-Rad Model 785 Vacuum Blotter) in 0.4 M NaOH to Gene Screen Plus Hybridization Transfer Membrane (NEN Research Products, Boston, Mass.). Nucleic acids were fixed to membranes by UV crosslinking in a UV-Stratalinker (Stratagene, Inc., La Jolla, Calif.), and the membranes were blocked in hybridization buffer (50% formamide, 5×SSC, 1% SDS, 10 mg/ml herring sperm DNA) at 42° C. for 2 h. The membranes were hybridized at 42° C. for 16 h in hybridization buffer with $10^7$ cpm of a 220 bp Kpn-HincII fragment from ECDIIIa cDNA labelled with ($\alpha$-$^{32}$P)dCTP (NEN Life Sciences) using a Random Prime DNA Labelling Kit (Boehringer Mannheim).

Templates were amplified in a Perkin Elmer GeneAmp PCR System 2400 (Perkin Elmer Cetus, Emeryville, Calif.) using the Expand High Fidelity PCR System (Boerhinger Mannheim) with 1×High Fidelity PCR buffer containing 2.5 mM $MgCl_2$, 5 $\mu$M of each primer, and 200 $\mu$M dNTPs. All primers were obtained from GIBCO BRL (Life Technologies). Numbering of nucleotide and amino acid residues is according to the HER-2 cDNA sequence reported by Coussens et al. (Coussens et al., Science 230:1132–1139, 1985). The HER-2 extracellular domain was targeted for amplification from an SKOV-3 cDNA library (Origene Technologies, Inc.) using a forward primer (A) identical to nucleotides (nt) 142–161 of HER-2 cDNA (5'-TGAGCACC <u>ATG</u>GAGCTGGC-3' [SEQ ID NO 3]), which spans the initiation codon (underlined) and a reverse primer (B) (5'-TCCGGCAGAAATGCCAGGCTCC-3' [SEQ ID NO 4]), which is complementary to HER-2 exon sequence at nt 1265–1286. Cycling parameters were: 94° C., 30 sec; 58° C., 45 sec; 68° C., 3 min, for 30 cycles. The region spanning the alternative sequence (denoted ECDIIIa) from genomic DNA, was amplified using a forward primer (C) (5'-AACACAGCGGTGTGAGAAGTGC-3' [SEQ ID NO 5]) identical to HER-2 exon-specific sequence at nt 1131–1152 and the reverse primer (B) [SEQ ID NO. 4] on DNA prepared as described (Bond et al., FEBS Letters 367:61–66, 1995) with cycling parameters: 94° C., 30 sec; 62° C., 30 sec; 72° C., 60 sec, for 25 cycles.

Reverse transcriptase-polymerase chain reaction (RT-PCR) was used to investigate the structure of mRNA containing the ECDIIIa sequence. First strand cDNA was reverse transcribed (Bond et al., FEBS Letters 367:61–66, 1995) using 5 $\mu$g RNA primed with 0.5 $\mu$g oligo-dT. To amplify the ECDIIIa insert and adjacent 5' HER-2 exon sequence, a forward primer (A) described above and a reverse primer (D) (5'-ATACCGGGACAGGTCAACAGC-3' [SEQ ID NO 6]) which is complementary to the 3'ECDIIIa-specific sequence were used. Cycling parameters were: 94° C., 30 sec; 60° C., 40 sec; 68° C., 2 min, for 30 cycles.

Amplification of the ECDIIIa insert and adjacent 3' HER-2 exon-specific sequence was with a forward primer (E) (5'-TCTGGGTACCCACTCACTGC-3' [SEQ ID NO 7]) which is identical to the 5'ECDIIIa-specific sequence and contains a Kpn1 restriction site and a reverse primer (F) (5'-T<u>TC</u>ACACTGGCACGTCCAGACC-3' [SEQ ID NO 8]) which is complementary to HER-2 exon sequence at nt 3898–3919 and spans the termination codon (underlined). Cycling parameters were: 94° C., 30 sec; 60° C., 40 sec; 68° C., 5 min, for 30 cycles.

The PCR product was subcloned and the nucleotide sequence was determined.

The results showed that the normal HER-2 coding sequence was present beginning with the 5' primer sequence and continued uninterrupted through nucleotide 1171. At this position, a 274 nucleotide insertion was found, followed by the expected coding sequence, including the 3' primer sequence. Analysis of the predicted protein product showed that the 274 nucleotide insertion encodes an extension of the known HER-2 protein, beginning at residue 340 (Coussens et al., *Science* 230:1132–1139, 1985), and introduces an in-frame stop codon 79 amino acids later (FIG. 1). Comparison of the inserted nucleotides and their predicted amino acid sequence with sequences in Genbank showed no homologies. Examination of the 5' and 3' junctions of the divergent sequence revealed consensus splice donor and acceptor sites (Sharp, and Burge, *Cell* 91:875–879, 1997) and include a pyrimidine tract and potential branchpoint adenine residues near the 3' end of the insert sequence (FIG. 1). Thus, the inserted sequence is likely to be an intron.

Inspection of the predicted amino acid sequence of the novel 79 amino acids [SEQ ID NO. 1] encoded by the inserted sequence shows a consensus N-linked glycosylation site and a high proline content of 19% (FIG. 1). The inserted sequence was designated ECDIIIa since it is located at the boundary between subdomains II and III in the extracellular domain of the p185HER-2 sequence (Lax et al., *Mol. Cell. Biol.* 8:1831–1834, 1988). The insert sequence is in-frame with the adjacent 5' HER-2 exon sequence for 236 nt where there is a termination codon.

EXAMPLE 2

This example provides the results from experiments characterizing ECDIIIa as contiguous with HER-2 exons in the genome. To investigate the HER-2 gene structure in the region of the ECDIIIa sequence, a forward primer, identical to nucleotides 763–785, and a reverse primer, complementary to nucleotides 1265–1286 of the HER-2 cDNA, were used in the PCR on human genomic DNA. The amplification product was anticipated to span exon 5 (Tal et al., *Mol. Cell. Biol.* 7:2597–2601, 1987) to an exon which is immediately 3' of the ECDIIIa sequence. Intron number and sizes were estimated based on PCR product sizes, restriction digest analysis, and partial sequence analysis of amplification products.

Next, human genomic DNA was examined using HER-2 exon-specific primers that directly flank the insert to determine the sequences immediately flanking the ECDIIIa sequence. A ~430 bp product was amplified from normal human genomic DNA and from genomic DNA extracted from carcinoma cell lines SKOV-3, SKBR-3 and BT474, all of which have HER-2 gene amplification (Kraus et al., *EMBO J.* 6:605–610, 1987) and were found to express ECDIIIa in their cDNA. The identities of the PCR products as HER-2 were verified by Southern blot analysis using the procedure described in Example 1. Nucleotide sequence analysis showed that the PCR product from human genomic DNA contained the ECDIIIa insert, flanked immediately on both sides by known HER-2 coding sequence; no mutations or rearrangements were seen. These data show that the ECDIIIa sequence represents a wholly retained intron, likely intron 8 based on the size of products amplified following intron 4 and on the location of intron 8 in the homologous EGFR gene and HER-3 gene (Lee and Maihle, *Oncogene* 16:3243–3252, 1998).

EXAMPLE 3

This example shows that ECDIIIa is the only retained intron within the coding sequence of HER-2 mRNA. To determine whether additional introns were retained in the mRNA containing the ECDIIIa insert sequence, the reverse transcriptase-polymerase chain reaction (RT-PCR) was employed. First, a forward primer identical to 5' HER-2 cDNA sequence at 142–161 which spans the initiation codon, and a reverse primer complementary to the 3' ECDIIIa sequence were employed with SKBR-3 and SKOV-3 cDNA. A product of 1.3 kb was amplified, which is the size expected if the product contained no introns other than intron 8. Amplification of the 3' HER-2 coding sequence was then performed using a forward primer identical to 5' ECDIIIa sequence and a reverse primer complementary to 3'HER-2 cDNA sequence at nucleotides 3898–3919, which spans the p185HER-2 termination codon. A product of 2.9 kb was amplified, which is the size expected from the HER-2 cDNA if no additional introns were retained.

Further characterizations of both the 5' (1.3 kb) and 3' (2.9 kb) amplification products by restriction digest analysis and nucleotide sequencing confirmed the absence of additional retained introns. To determine the size of the products amplified when intron sequences are included, genomic DNA was used as a template for the PCR reactions, which resulted in products of approximately 10 kb for the 5' coding sequence and 5 kb for the 3' coding sequence. These results indicate that the alternative HER-2 transcript, resulting from retention of an intron of 274 bp, was expected to be about 4.8 kb in size, assuming that the 5'untranslated (5'UTR) and 3' untranslated (3'UTR) regions are identical in size to the previously described ~4.5 kb HER-2 cDNA (Coussens et al., *Science* 230:1132–1139, 1985).

EXAMPLE 4

This example illustrates the expression of a protein containing an ECDIIIa sequence. To assess whether the alternative sequence is translated into a protein product, the ECDIIIa sequence was expressed as a polyhistidine-tagged peptide in bacteria, purified the peptide by nickel-affinity chromatography, and raised antisera against the purified peptide. Briefly, the bacterial expression vector was prepared by amplifying the ECDIIIa sequence from the SKOV-3 cDNA library using primer E and a reverse primer complementary to the 3' end of the ECDIIIa insert sequence. The reverse primer contained a BamH1 restriction site sequence, and was identical to that used for template construction in the RPA (described in examples 1 and 2). The PCR amplification product of ~280 bp was digested with Kpn1 and BamH1, gel purified (Qiaex II, Qiagen, Chatsworth, Calif.), and cloned into the pET30a vector, which encodes a six histidine tag at the amino-terminus of the expressed protein (Novagen, Madison, Wis.). The resulting expression vector, pET-ECDIIIa, was used for transformation of bacterial strain BL21.

To express the ECDIIIa protein product, BL21 cells transformed with the pET-ECDIIIa expression vector were grown in LB broth with 30 μg/ml Kanamycin for 4 h at 37° C.. Expression was induced with 0.1 mM IPTG for 3 h and the harvested cells were lysed by sonication, and then centrifuged at 39,000×g for 20 min. The supernatant was absorbed onto Ni-NTA agarose (Qiagen), by shaking for 60 min at room temperature. The resin was washed with ten volumes of wash buffer (10 mM Tris pH 7.9 and 300 mM NaCl), followed by ten volumes of wash buffer with 50 mM imidazole. The his-tagged ECDIIIa protein was eluted in wash buffer with 250 mM imidazole. The his-tagged protein, which was estimated to be approximately 90% pure by Coomassie Blue staining of gels, was used to generate and characterize antibodies.

Briefly, anti-ECDIIIa antisera were produced by Cocalico Biologicals, Inc. (Reamstown, Pa.) by injection of two rabbits with purified polyhistidine-tagged ECDIIIa peptide (described below). Polyclonal anti-neu (N) was produced against a peptide identical to amino acid residues 151–165 of p185HER-2 (Lin and Clinton, Oncogene 6:639–643, 1991). Polyclonal anti-neu (C) was made against a peptide identical to the last 15 residues of the carboxy-terminus of p185HER-2 (Lin et al., Mol. Cell. Endocrin. 69:111–119, 1990). Antisera from two immunized rabbits were characterized and found to contain antibodies of high titer that reacted with the purified ECDIIIa peptide.

A Western blot analysis examined whether SKBR-3 cells, which expressed the alternative sequence in its cDNA, produced a protein that reacts with anti-ECDIIIa antibody. A 68 kDa protein from the cell extract and from the extracellular media reacted with anti-ECDIIIa antibody from two different rabbits diluted at least 20,000 fold, but not with preimmune sera. Inspection of the cDNA sequence of the alternative transcript (FIG. 1) predicted a secreted protein product of 65–70 kDa if all 5 consensus N-linked glycosylation sites in the N-terminal p185HER-2 sequence were glycosylated (Stern et al., Mol. Cell. Biol. 6:1729–1740, 1986).

If the 68 kDa ECDIIIa protein [SEQ ID NO. 2] is the translation product of the alternative HER-2 mRNA, then its N-terminal residues should be identical to the N-terminal 340 residues of p185HER-2. Therefore, cell extract from SKBR-3 cells was immunoprecipitated with anti-peptide antibody against an N-terminal sequence of HER-2, anti-neu (N) (Lin and Clinton, Oncogene 6:639–643, 1991) or with anti-ECDIIIa, and the immune complexes were examined by Western blot analysis with both antibodies. Briefly, three to 5 µl of antisera were added to 2 mg of protein from cell lysates prepared in M-RIPA buffer (1% Nonidet P-40, 50 mM Tris pH 7.4, 0.1% sodium deoxycholate, 150 mM NaCl, 1 mM PMSF, 1% aprotinin), which had been centrifuged to remove nuclei. Immunoprecipitation was for 2 h with shaking at 4° C. as described (Lin et al., Mol. Cell. Endocrin. 69:111–119, 1990). The immune complexes were bound to Protein G Sepharose (Pharmacia) by incubation for 1 h at 4° C. with shaking, collected by centrifugation, and washed four times with M-RIPA. The proteins were released from the immune complex by incubation at 95° C. for 2 min in SDS-PAGE sample buffer and resolved by SDS-PAGE in 7.5% gels (Mini-Protean II electrophoresis cell, Bio-Rad).

Western blotting was conducted following SDS-PAGE. Proteins were electroblotted onto nitrocellulose (Trans-blot, BioRad) using a semi-dry transfer unit (Bio-Rad) at 15 V for 20 min per gel (0.75 mm thick) equilibrated with 25 mM Tris pH 8.3, 192 mM glycine, 50 mM NaCl, and 20% methanol. The membranes were blocked with 5% nonfat dry milk at 25° C. for one hour. The blots were then incubated with primary antibody, washed twice for 15 min, and four times for 5 min with TBS-Tween (Tris-buffered saline containing 0.05% Tween), and then incubated for 40 min with goat anti-rabbit secondary antibody, conjugated to horseradish peroxidase (Bio-Rad), diluted 1:10,000 in TBS-Tween. After incubation with secondary antibody, the membranes were washed as described above and reacted with chemiluminescent reagent (Pierce) and then were exposed to Kodak X-OMAT BLU film.

As expected, p68HER-2 was detected when anti-ECDIIIa was used for immunoprecipitation and for Western blot analysis. When anti-ECDIIIa was used for immunoprecipitation and anti-neu (N) was the probe in the Western blot, a 68 kDa protein was detected, indicating that p68ECDIIIa contained the N-terminal sequence of p185HER-2. Further, anti-neu (N) precipitated p68HER-2, which was detected by probing with anti-ECDIIIa antibody. These results demonstrate that p68HER-2 contains both ECDIIIa and the N-terminal sequence of HER-2.

Several other cell lines were examined for expression of p68ECDIIIa. The carcinoma cell lines which contained ECDIIIa sequence in their cDNA (BT474, SKOV-3) also had p68HER-2. Of several cell lines examined, HEK293 cells, derived from normal human embryonic kidney cells, expressed the highest levels of p68ECDIIIa in the cell extract and in the extracellular media, at about 5 to 10-fold higher amounts than SKBR-3 cells. In comparison to the carcinoma cell lines examined (SKBR-3, SKOV-3, and BT474) which overexpress p185HER-2, the HEK293 cells contained about 20 fold lower amounts of p185HER-2. Therefore, the relative proportion of p68HER-2 to p185HER-2 was at least 100 fold greater in HEK293 cells than in the three carcinoma cell lines studied. Reactivity with p68HER-2 as well as with a protein of ~120 kDa, particularly apparent in the HEK293 extracts, was blocked by preincubation of the antisera with purified ECDIIIa peptide demonstrating sequence-specific reactivity. The larger protein may be a dimer of p68HER-2. Therefore, p68HER-2 was expressed and secreted from several carcinoma cell lines and is at 5–10 fold elevated levels in HEK293.

EXAMPLE 5

This example illustrates expression of an alternative HER-2 transcript containing the ECDIIIa intron sequence. Results of the RT-PCR analysis indicated that the ECDIIIa sequence was inserted into an otherwise normal-sized HER-2 mRNA. These data suggest an alternative transcript of ~4.8 kb. To examine the size and expression of the ECDIIIa alternative transcript, Northern blot analysis was conducted using an ECDIIIa-specific probe. Briefly, a template for antisense RNA probe synthesis was constructed from SKOV-3 cDNA by PCR amplification of a 389 bp sequence spanning the entire ECDIIIa insert sequence and containing adjacent 5'HER-2 exon sequence. The PCR was done using the forward primer C [SEQ ID NO. 5] that is identical to HER-2 cDNA sequence at nt 1131–1152 and a reverse primer (5'-GCACGGATCCATAGCAGACTGAG GAGG-3' [SEQ ID NO. 9]) which contains a 3' BamH1 restriction endonuclease site and is complementary to the sequence spanning the 3' splice site of the ECDIIIa sequence. The PCR product was then digested with BamH1, liberating a 375 bp fragment, which was cloned into pBluescript SK (Stratagene). The plasmid was sequenced by the Vollum Institute Core Sequencing Facility (Portland, Oreg.) with m13 forward and reverse primers. An antisense RNA probe complimentary to the entire ECDIIIa sequence and to 87 nt of HER-2 exon sequence 5' to the insert was transcribed from 1 µg of linearized template using ($\alpha$-$^{32}$P) CTP, T7 RNA polymerase, and the T7/SP6 Riboprobe Synthesis System (Promega, Madison, Wis.). This probe was expected to protect a 370 nt fragment when hybridized with mRNA containing ECDIIIa and adjacent HER-2 exon sequence, and to protect an 87 nt fragment when hybridized with fully spliced HER-2 mRNA.

To prepare the RNA hybrids, 30 µg of RNA were hybridized with approximately 50,000 cpm of antisense RNA probe at 48° C. for 16 h. RNA hybrids were digested for 30 min at 37° C. with 40 µg/ml RNaseA (Boerhinger Mannheim) and 2 µg/ml RNase T1 (Life Technologies) in a solution of 250 mM NaCl, 5 mM EDTA, and 10 mM Tris pH 7.5. Proteinase K (100 μg) (Life Technologies) in 20 μl 10% SDS was added to stop the digestion. Samples were extracted with acid phenol (pH 4.5; Life Technologies) and chloroform, precipitated with two volumes of 100% ethanol, and suspended in 5 μl of RPA sample buffer (88% formamide, 10 mM EDTA pH 8.0, 1 mg/ml xylene cyanol, and 1 mg/ml bromophenol blue). Samples were denatured at 95° C. for 10 min and electrophoresed on a 5% polyacrylamide/urea gel in TBE (89 mM Tris, 89 mM borate, 2 mM EDTA pH 8.3). Gels were dried under vacuum and subjected to phosphorimager analysis for quantitation of the protected fragments (IP Lab Gel, Molecular Dynamics).

An alternative transcript of approximately 4.8 kb was detected in HEK293 cells which expressed the highest levels of p68ECDIIIa. However an alternative transcript could not be detected by Northern analysis of the SKBR-3, BT474, or SKOV-3 carcinoma cell lines. Therefore, the more sensitive ribonuclease protection assay (RPA) was employed to examine the expression levels of the alternative transcript relative to the filly spliced 4.5 kb transcript. RNA from ovarian (SKOV-3) and breast (SKBR-3 and BT474) carcinoma cell lines, which contained detectable levels of p68ECDIIIa, and a control cell line, 17-3-1, stably transfected with HER-2 cDNA, were hybridized with an antisense $^{32}$P-labeled RNA probe which spanned the entire ECDIIIa (intron 8) sequence and 5' HER-2 exon sequence flanking intron 8. Following RNase digestion, electrophoresis, and autoradiography, a band of 370 nucleotides was detected in each cell line except for 17-3-1, which corresponds to the expected size protected by an ECDIIIa-containing HER-2 mRNA. In addition, an 87 nucleotide protected fragment was detected in all cells and is the size expected for the fully-spliced HER-2 message which is overexpressed by more than 100 fold in these carcinoma cell lines compared to normal control cell lines (Kraus et al., *EMBO J.* 6:605–610, 1987). The amounts of each protected fragment were quantitated and normalized for size to estimate the relative abundance of the alternative transcript, expressed as a percentage of the p185HER-2 mRNA. The alternative HER-2 mRNA with the ECDIIIa insert was at 4.2% the level of the fully spliced transcript in SKOV-3; 5.4% in SKBR-3, and 0.8% in BT474 cells.

EXAMPLE 6

This example shows that alternative transcripts containing the ECDIIIa insert were expressed in human embryonic kidney and liver. A Northern blot was conducted to examine whether an alternative transcript, which contains the ECDIIIa sequence, was expressed in normal human tissue. PolyA$^+$mRNA from a variety of human fetal tissues prepared as a Northern blot was hybridized with a radiolabeled probe specific for the unique ECDIIIa sequence. A 4.8 kb mRNA was detected in kidney and a 2.6 kb transcript was detected in liver (FIG. 2). The 4.8 kb transcript likely corresponded to the full length 4.5 kb transcript with the 274bp insert and the 2.6 kb transcript may have corresponded to a previously described 2.3 kb alternative transcript (Yamamoto et al., *Nature* 319:230–234, 1986; and Scott et al., *Mol. Cell. Biol.* 13:2247–2257, 1993) with the 274bp ECDIIIa insert. When the blot was stripped and hybridized with a probe specific for the 5' HER-2 coding sequence, a broad band representing the 4.8 and 4.5 kb mRNAs was detected in fetal kidney tissues and the truncated 2.6 kb transcript was detected in liver showing that these alternative transcripts contain sequences that encode the HER-2 ECD. Because the inserted ECDIIIa sequence contained a termination codon, the same protein product may be produced from each of these mRNAs.

Several cell lines were also investigated for the ECDIIIa-containing alternative transcript by Northern blot analysis. The 4.8 kb alternative transcript was detected in the human embryonic kidney cell line, HEK-293 (FIG. 2). Although the ECDIIIa sequence was detected by RT-PCR analysis of SKBR-3, BT474, and SKOV-3 carcinoma cell lines, which all contain HER-2 gene amplification, an ECDIIIa-containing alternative transcript could not be detected by Northern analysis of these cells. Therefore, the more sensitive ribonuclease protection assay (RPA) was employed using an antisense probe which spanned the entire ECDIIIa sequence and 5' HER-2 exon sequence flanking the ECDIIIa sequence. The alternative HER-2 mRNA with the ECDIIIa insert was detected at less than 5% of the fully spliced transcript in SKOV-3, SKBR-3, and BT474 cells. These findings show that two alternative transcripts containing the ECDIIIa sequence were expressed in a tissue-specific manner in normal human tissues, that the 4.8 kb alternative transcript was expressed in the HEK-293 cell line, and that the carcinoma cells with gene amplification express reduced amounts of the alternative transcript at less than 5% of the 4.5 kb HER-2 transcript.

EXAMPLE 7

This example illustrates expression of a protein containing the ECDIIIa sequence. To assess whether the alternative sequence was translated into a protein product, the ECDIIIa sequence, as a polyhistidine-tagged peptide in bacteria, was expressed and purified by nickel-affinity chromatography, and raised antisera against the purified peptide. The HEK-293 cells, which expressed the 4.8 kb ECDIIIa alternative transcript, were examined for expression of an ECDIIIa-containing protein by Western analysis. A 68 kDa protein from the cell extract and from the extracellular media reacted with the anti-ECDIIIa antibody (FIG. 3) but not with preimmune sera and reactivity was blocked by preincubation of the antisera with purified ECDIIIa peptide (FIG. 3). The larger protein of ~125 kDa detected in some cell extracts may be an aggregate of p68HER-2. The cDNA sequence of the alternative transcript (FIG. 1) predicts a secreted protein product of 65–70 kDa if all 5 consensus N-linked glycosylation sites in the N-terminal p185HER-2 sequence are glycosylated (Stern et al., *Mol. Cell. Biol.* 6:1729–1740, 1986). Several other cell lines were examined for expression of p68ECDIIIa. The carcinoma cell lines which contained ECDIIIa sequence in their cDNA (BT474, SKOV-3, SKBR-3) also had detectable levels of p68HER-2.

EXAMPLE 8

Figure 4:
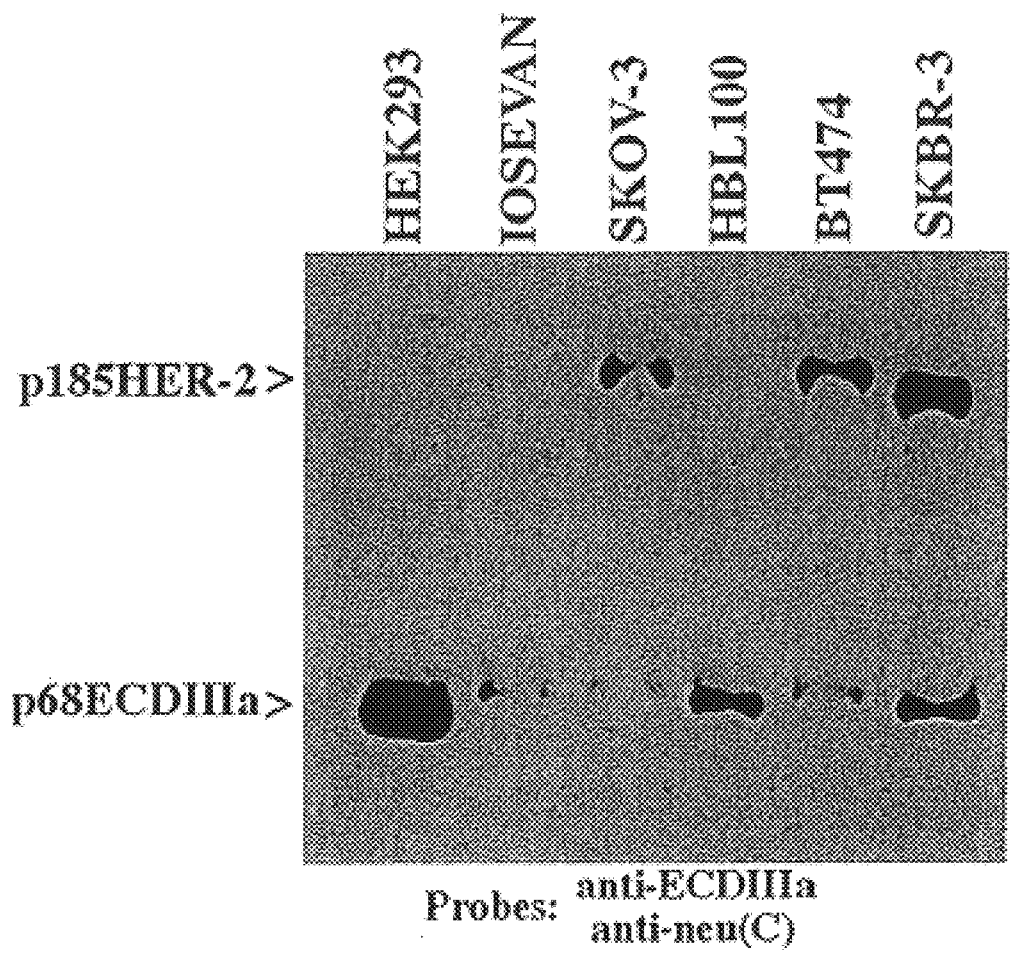
FIG. 4 shows the expression of p185HER-2, relative to p68ECDIIIa expression, is markedly elevated in carcinoma cell lines in which the HER-2 gene is amplified. Cell extracts (15 μg of protein) from human embryonic kidney cell line (HEK293), nontumorigenic ovarian surface epithelial cell line (IOSEVAN), ovarian carcinoma cell line with HER-2 gene amplification (SKOV-3), nontumorigenic breast epithelial cell line (HBL100), and breast carcinoma cell lines with HER-2 gene amplification (BT474 and SKBR-3), were resolved by SDS-PAGE in 7.5% acrylamide gels and analyzed as a Western blot. The Western blot was probed with both antibodies specific for p68HER-2 (anti-ECDIIIa) and for p185HER-2 (anti-neu(C)).

This example illustrates the expression of p68HER-2 relative to p185HER-2 was markedly reduced in carcinoma cell lines in which the HER-2 gene is amplified. Because the p68HER-2 mRNA was expressed at very low levels relative to the p185HER-2 mRNA in carcinoma cell lines with HER-2 gene amplification, the relative proportions of p68HER-2 and p185HER-2 proteins in several cell lines were examined with and without HER-2 gene amplification. Western blots were prepared and probed with both antisera specific for p68HER-2 and for p185HER-2. FIG. 4 shows that p185HER-2 was readily detected in the carcinoma cells lines that have their HER-2 gene amplified about 8 times (Kraus et al., *EMBO J.* 6:605–610, 1987). However, there was not a corresponding elevation in p68HER-2. In comparison, p68HER-2 was the only HER-2 protein detected in the HEK-293, IOSEVAN, and HBL100 nontumorigenic cells, although p185HER-2 was expressed at very low levels in these cells (Kraus et al., *EMBO J.* 6:605–610, 1987) and was detected in overexposed blots. These data show that p68HER-2 was low in proportion to p185HER-2 in carcinoma cells with HER-2 gene amplification and suggests that a mechanism may exist to maintain low levels of p68HER-2 when p185HER-2 is overexpressed.

EXAMPLE 9

This example illustrates that p68HER-2 and the ECDIIIa peptide specifically bind to p185HER-2. Because p68HER-2 is secreted and contains subdomains I and II identical to p185HER-2, in addition to a novel sequence, the possibility that p68HER-2 may interact with p185HER-2 was investigated. Antipeptide antibody against the N-terminus of p185HER-2 and p68HER-2, anti-neu (N), or antibody specific for p185HER-2, anti-neu(C), were used for immunoprecipitations of SKBR-3 carcinoma cells, which express low levels of p68HER-2 and overexpress p185HER-2. The immunoprecipitated material was prepared as a Western blot and probed with both anti-ECDIIIa specific for p68HER-2 and with anti-neu(C). Anti-neu (N) immunoprecipitated both p68HER-2 and p185HER-2 (FIG. 5A). In addition, antibodies specific for the C-terminus of p185HER-2 immunoprecipitated p185HER-2 and coprecipitated p68HER-2 (FIG. 5A), suggesting an interaction between the two proteins.

Since binding interactions between ECD sequences are very weak (Tzahar et al., *EMBO J.* 16:4938–4950, 1997; Fitzpatrick et al., *FEBS Letters* 431:102–106, 1998), the possibility that binding may be conferred by the novel proline rich ECDIIIa domain was examined. The unique 79 amino acid domain, purified as a His-tagged protein, was immobilized on nickel agarose and used in a pull-down assay. For controls, two purified His-tagged peptides unrelated to ECDIIIa, a 600 residue fragment of the Wilson's disease membrane protein, and a 70 residue fragment containing the DNA binding domain of the CREB protein, were likewise immobilized on nickel agarose resin. The immobilized peptides were incubated with protein extracts prepared from HER-2 transfected 3T3 cells (17–3–1). Following extensive washes, the bound proteins were eluted and prepared as a Western blot which was probed with an antibody specific for p185HER-2. Equal amounts of His-tagged ECDIIIa peptide and control peptide were bound to the resin as confirmed by elution with 1M imidazole and Coomassie staining of the eluted material in SDS-gels. While no p185HER-2 was retained by resin without peptide or with control peptide, p185HER-2 was selectively retained by the ECDIIIa peptide (FIG. 5B).

Since the ECDIIIa domain bound to p185HER-2 in a pull down assay, the question of whether the ECDIIIa domain preferentially binds to cells that overexpress p185HER-2 was examined. This was investigated using monolayer cultures of 17-3-1 cells transfected with HER-2 compared to the parental 3T3 cells. The cells were incubated with different concentrations of the His-ECDIIIa peptide, washed, and extracted in denaturing buffer with protease inhibitors. To detect any bound peptide, the cell extracts were examined by Western blot analysis using antibodies specific for ECDIIIa. In addition, equal aliquots of the ECDIIIa peptide treated cells were reacted as a Western blot with antibodies specific for p185HER-2, demonstrating the overexpression of p 185HER-2 in the transfected 17-3-1 cells. The ECDIIIa peptide preferentially bound to intact 17-3-1 cells at nM concentrations (FIG. 5C) whereas little or no peptide was found to bind to equivalent amounts of parental 3T3 cells suggesting a specific interaction with the extracellular domain of p185HER-2.

EXAMPLE 10

Figure 6:
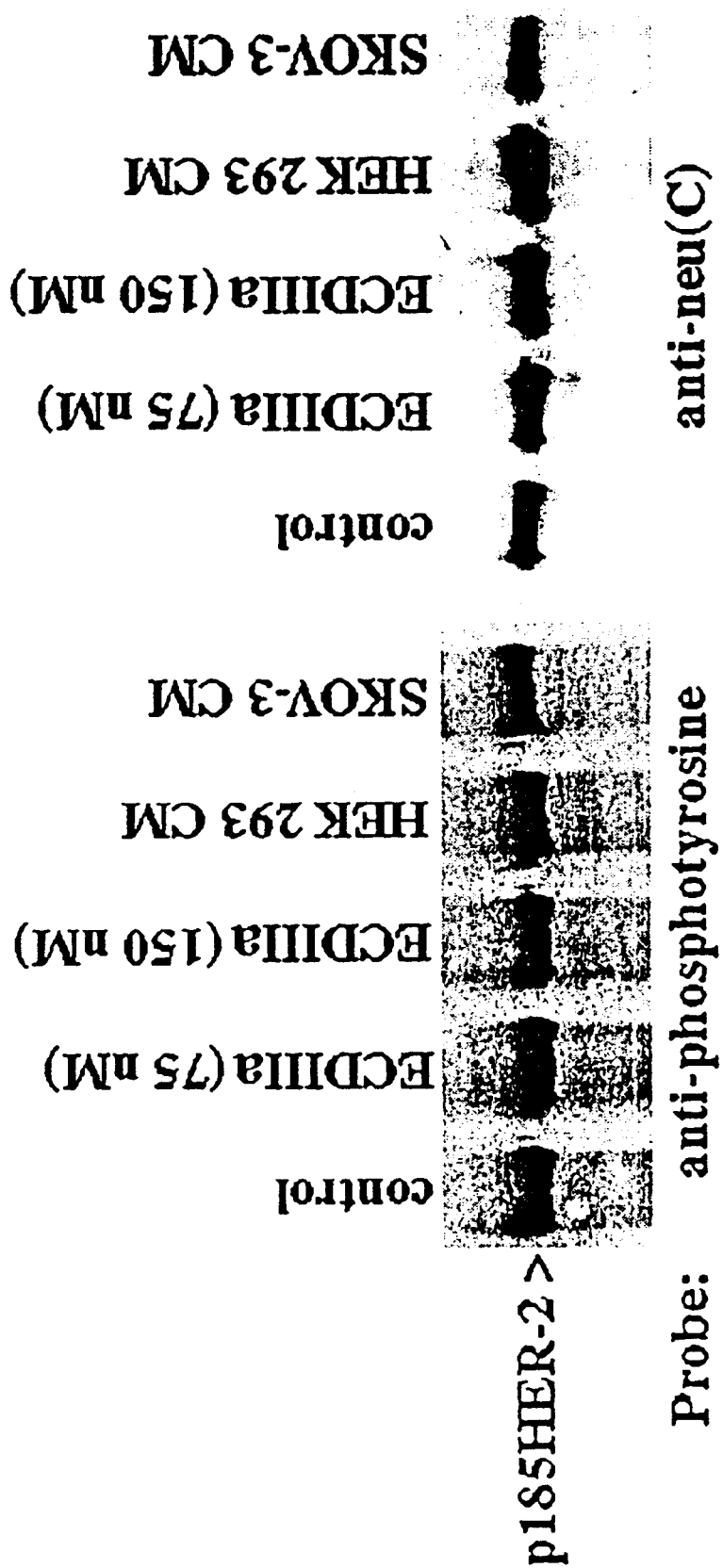
FIG. 6 shows that neither p68-rich conditioned media nor the ECDIIIa peptide stimulate tyrosine phosphorylation of p185HER-2. Monolayer cultures of ~10$^5$ HER-2 transfected 17-3-1 cells were washed twice with PBS, incubated in serum-free media at 37° C. for 24 hrs, and then treated for 10 minutes with 75 or 150 μM His-tagged ECDIIIa or with 50×CM from HEK-293 cells that secrete high levels of p68 or 50×CM from SKOV-3 cells that have no detectable p68HER-2. The treated cells were extracted with denaturing buffer containing the phosphotyrosine phosphatase inhibitor vanadate (2 mM) and 20 μg/ml of cell extract protein from each sample were analyzed by Western blot analysis with monoclonal antibodies against phosphotyrosine (Sigma). The blot was stripped by incubation at 55° C. for 30 min in 62.5 mM Tris pH 6.7, 2% SDS, and 100 mM 2-mercaptoethanol and then reprobed with anti-neu(C) specific for p185HER-2.

Effect of p68ECDIIIa and the ECDIIIa peptide on tyrosine phosphorylation of p185HER-2 was examined. Tyrosine phosphorylation of RTKs is the initial indication of ligand activation and signal transduction. Tyrosine phosphorylation in 17-3-1 cells treated with different amounts of the purified ECDIIIa peptide, with conditioned media (CM) from HEK293 cells that contained high levels of p68HER-2 (FIG. 2A), or with control, conditioned media from SKOV-3 cells that had no detectable p68HER-2 were examined. There was no increase in the tyrosine phosphorylation signal at 10 minutes (FIG. 6) or 2 hrs of treatment with His-ECDIIIa or with concentrated CM suggesting that p 185HER-2 was not activated. Neither p68HER-2-containing CM nor the ECDIIIa peptide detectably altered the phosphotyrosine signal corresponding to p185HER-2 from SKOV-3 cells in which p185HER-2 tyrosine phosphorylation levels were low. Additionally, p68HER-2 and the ECDIIIa peptide had no discernable effect on in vitro self-phosphorylation activity of p185HER-2 immunoprecipitated from 17-3-1 cell extracts. These results support the conclusion that p68HER-2 did not activate p185HER-2 signal transduction.

---

We claim:

1. An isolated nucleic acid comprising a sequence that encodes a polypeptide comprising the amino acid sequence of SEQ ID NO:1, or a fragment of SEQ ID NO:1 of about 50 to 79 contiguous residues in length, wherein the polypeptide binds to the extracellular domain (ECD) of HER-2 with an affinity binding constant of at least $10^8$ $M^{-1}$.

2. The isolated nucleic acid of claim 1, wherein the polypeptide is from about 69 to 79 contiguous residues in length.

3. The isolated nucleic acid of claim 1, wherein the polypeptide binds to a site on the extracellular domain (ECD) of HER-2 that is, at least in part, distinct from the site of binding of the 4D5 humanized monoclonal antibody (HERCEPTIN®).

4. A transfected cell comprising an expression vector comprising a nucleic acid that encodes a polypeptide of SEQ ID NO:1 of about 50–79 contiguous amino acid residues in length, wherein the polypeptide binds to the extracellular domain (ECD) of HER-2 with an affinity binding constant of at least $10^8$ $M^{-1}$.

5. An isolated nucleic acid comprising a sequence that encodes a polypeptide comprising the amino acid sequence of SEQ ID NO:2, or a fragment of SEQ ID NO:2 of about 80 to 419 contiguous residues in length, wherein the C terminal 79 contiguous amino acids are present, wherein at least one N-linked glycosylation site is present, and wherein the polypeptide binds to the extracellular domain (ECD) of HER-2 with an affinity binding constant of at least $10^8$ $M^{-1}$.

6. The isolated nucleic acid of claim 5, wherein the polypeptide is from about 350 to 419 residues in length and three N-linked glycosylation sites are present.

7. A transfected cell comprising an expression vector comprising a nucleic acid that encodes a polypeptide of SEQ ID NO:2 of about 80 to 419 contiguous residues in length, wherein the C terminal contiguous 79 amino acids are present, wherein at least one N-linked glycosylation site is present, and wherein the polypeptide binds to the extracellular domain (ECD) of HER-2 with an affinity binding constant of at least $10^8$ $M^{-1}$.

* * * * *

UNITED STATES PATENT AND TRADEMARK OFFICE
CERTIFICATE OF CORRECTION

PATENT NO. : 6,414,130 B1
DATED : July 2, 2002
INVENTOR(S) : Doherty et al.

It is certified that error appears in the above-identified patent and that said Letters Patent is hereby corrected as shown below:

<u>Title page</u>,
Item [75], Inventor, should read -- Joni Kristen Doherty, Gail M. Clinton, John P. Adelman, all of Portland, Or. (US) --

Signed and Sealed this

Sixth Day of July, 2004

JON W. DUDAS
*Acting Director of the United States Patent and Trademark Office*